United States Patent
Wu et al.

(10) Patent No.: US 6,703,514 B2
(45) Date of Patent: Mar. 9, 2004

(54) 4-THIO COUMARINS

(75) Inventors: Jie Wu, Ridgewood, NJ (US); Zhen Yang, Ridgewood, NJ (US); Reza Fathi, Hohokus, NJ (US); Qiang Zhu, Ridgewood, NJ (US); Lisha Wang, Ridgewood, NJ (US)

(73) Assignee: Vivo Quest, Inc., Valley Cottage, NY (US)

( * ) Notice: Subject to any disclaimer, the term of this patent is extended or adjusted under 35 U.S.C. 154(b) by 0 days.

(21) Appl. No.: 10/437,768

(22) Filed: May 13, 2003

(65) Prior Publication Data

US 2004/0002538 A1 Jan. 1, 2004

Related U.S. Application Data

(60) Provisional application No. 60/380,487, filed on May 14, 2002.

(51) Int. Cl.⁷ ............................................. C07D 311/02
(52) U.S. Cl. ........................................ 549/284; 549/285
(58) Field of Search ................................. 549/284, 285

(56) References Cited

U.S. PATENT DOCUMENTS 5,563,280 A  * 10/1996  Alvarado et al. ........... 549/285
5,681,968 A  * 10/1997  Alvarado et al. ........... 549/285

* cited by examiner

*Primary Examiner*—Amelia Owens
(74) *Attorney, Agent, or Firm*—Kenyon & Kenyon

(57) ABSTRACT

4-thio substituted coumarin derivatives and coumarin dimers are provided, as well as processes for their preparation. A synthetic process for the preparation of 4-thio substituted coumarin derivatives is provided using mild reaction conditions, which maintains a high substituent tolerance and is appropriate for use in solid phase syntheses for producing a library of 4-thio substituted coumarin derivatives for biological screening.

26 Claims, No Drawings

4-THIO COUMARINS

This Application claims benefit of Provisional Application 60/380,487 May 14, 2002.

FIELD OF THE INVENTION

The present invention relates to novel 4-thio substituted coumarin derivatives and coumarin dimers, and processes for their preparation. The invention provides a synthetic process for the preparation of 4-thio substituted coumarin derivatives using mild reaction conditions, which provides a high substituent tolerance and is appropriate for use in solid phase syntheses for producing a library of 4-thio substituted coumarin derivatives for biological screening.

BACKGROUND OF THE INVENTION

Strategies in new drug discovery often look to natural products for leads in finding new chemical compounds with therapeutic properties. One of the recurring problems in drug discovery is the availability of organic compounds derived from natural sources. Techniques employing combinatorial chemistry attempt to overcome this problem by allowing the high throughput synthesis and testing of hundreds or thousands of related synthetic compounds, called a chemical library. In designing the synthesis of a prospective therapeutic compound or a chemical library, one often looks to natural chemical motifs which are known to have broad biological activity. Of particular interest are materials which have structural components, such as coumarins, flavones, and isoflavones, which are similar to secondary metabolites from plant extracts.

Coumarins are widely distributed in the plant kingdom. Approximately 50 naturally occurring coumarin derivatives have been identified. Derivatives of coumarin posses a range of biological activities. Of particular interest to researchers are modification at the 3- and 4-position of the coumarin scaffold and synthesis of symmetrical and unsymmetric dimers of coumarin compounds for biological evaluations. To avoid confusion, the coumarin derivatives described herein are numbered according to the following convention:

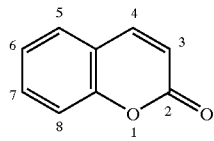

Unfortunately, the preparation of such coumarin derivatives has suffered from multiple difficulties. This is particularly true of 4-substituted thiol derivatives of coumarin. Although certain 4-thio coumarins have been prepared, their synthesis has involved harsh conditions (such as the use of stoichiometric amounts of strong bases or toxic reagents, often under high temperatures), multiple synthetic steps, and poor substituent tolerance. For example, Parfenov et al. discussed a route for synthesis of 4-coumarinyl sulfides derivatives from 4-tosyl coumarin using harsh reaction conditions or from 4-chloro coumarin, which was generated under acidic conditions and high temperature. Parfenov et al., *Khim. Gererotsikl. Soedin.*, 1991, 8, 1032. It is known that the selectivity of the reaction of 4-hydroxycoumarin with chlorinating reagents such as $PCl_5$ and $POCl_3$ is low, because a considerable amount of 4-chloro-3,4,3',4"-tercoumarin will be formed as a by-product. Also reported with regard to substituted 4-thio coumarin derivatives, is a paper by Martin Kovječ, in ARKIVOC, 2001, part (vi), which utilizes 4-chlorocoumarin as an intermediate to synthesize 4-ethylthiocoumarin under basic conditions at elevated temperature (reflux) using sodium ethanethiol. Although a high yield of product was obtained by this methodology, it is not applicable to the production of a large variety of 4-thiol substituted derivatives with a diverse substitution pattern because of the harsh reaction conditions (both acidic and basic) used to arrive at the product. Extension of this route to solid supported synthesis for production of a combinatorial library is limited due to the acid sensitivity of many common solid support linkers.

SUMMARY OF THE INVENTION

The present invention is directed to certain 4-thio substituted coumarin derivatives of the formula I

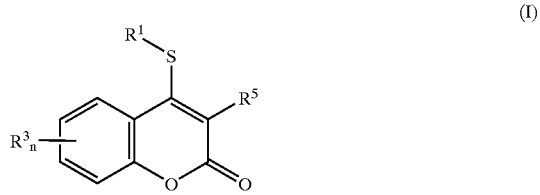

wherein
$R^1$ is selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
an unsubstituted or substituted alkyl group, wherein the substituted alkyl group may be substituted with one or more halogen, hydroxy, and lower alkoxy; and
an unsubstituted or substituted cycloalkyl group, wherein the substituted cycloalkyl group may be substituted with one or more halogen, hydroxy, and lower alkoxy;
$R^3$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^3$ is a group of the formula

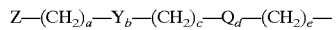

wherein Y and Q are independently selected from an aromatic group, O, S, —CR=CR—,

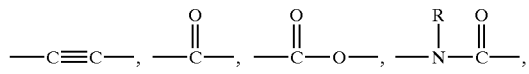

-continued

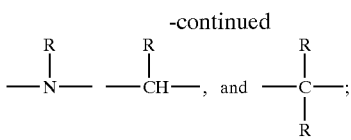

each R is independently selected from H or lower alkyl,

Z is selected from H, —$CO_2R$, —OR, —SR, —$NR_2$,

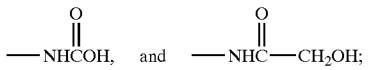

a, c and e are independently selected from values from 0 to 10;

b and d are independently selected from 0 and 1, provided that when a=0 then b=0, and when c=0 then d=0;

or $R^3$ may occupy two adjacent positions to form a fused aromatic ring, n is selected from values between 0 and 4;

$R^5$ is selected from hydrogen, lower alkyl, lower alkenyl, lower alkynyl, and lower aralkyl, each of which may be unsubstituted or substituted with one or more substituents selected from halogen, lower alkyl, and lower alkoxy, thio-lower alkyl, $C_1$–$C_8$ acyl, lower alkyl ester, amide, and lower alkyl amide; or $R^5$ may be a group of the formula

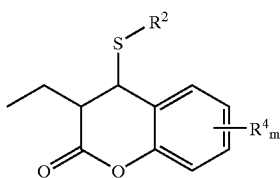

wherein $R^2$ is selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
an unsubstituted or substituted alkyl group, wherein the substituted alkyl group may be substituted with one or more halogen, hydroxy, and lower alkoxy; and
an unsubstituted or substituted cycloalkyl group, wherein the substituted cycloalkyl group may be substituted with one or more halogen, hydroxy, and lower alkoxy;

$R^4$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^4$ is a group of the formula Z-$(CH_2)_a$—$Y_b$—$(CH_2)_c$—$Q_d$—$(CH_2)_e$— wherein Y and Q are independently selected from an aromatic group, O, S, —CR=CR—,

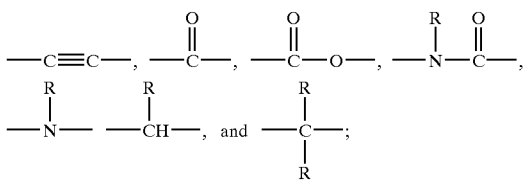

each R is independently selected from H or lower alkyl,

Z is selected from

H, —$CO_2R$, —OR, —SR, —$NR_2$,

a, c and e are independently selected from values from 0 to 10;

b and d are independently selected from 0 and 1, provided that when a=0 then b=0, and when c=0 then d=0;

or $R^4$ may occupy two adjacent positions to form a fused aromatic ring, and, m is selected from values between 0 and 4.

Therefore, the present invention provides for symmetrical and unsymmetrical dimeric forms of 4-thio-substituted coumarin derivatives of the formula II:

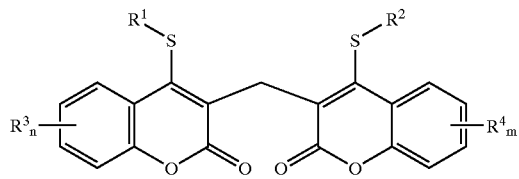

(II)

wherein $R^1$ and $R^2$ are independently selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
an unsubstituted or substituted alkyl group, wherein the substituted alkyl group may be substituted with one or more halogen, hydroxy, and lower alkoxy; and
an unsubstituted or substituted cycloalkyl group, wherein the substituted cycloalkyl group may be substituted with one or more halogen, hydroxy, and lower alkoxy;

each $R^3$ and $R^4$ is independently selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or is a group of the formula

wherein Y and Q are independently selected from an aromatic group, O, S, —CR=CR—,

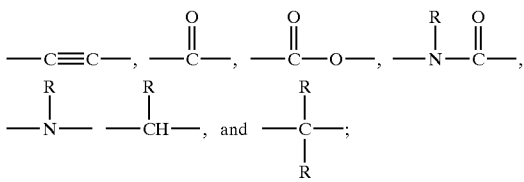

each R is independently selected from H or lower alkyl,

Z is selected from

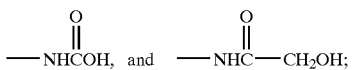

a, c and e are independently selected from values from 0 to 10;

b and d are independently selected from 0 and 1, provided that when a=0 then b=0, and when c=0 then d=0;

or $R^3$ or $R^4$ may occupy two adjacent positions to form a fused aromatic ring, n and m are independently selected from values between 0 and 4.

The invention also provides for 4-thio coumarin derivatives of the formula III:

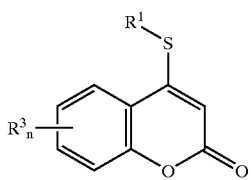

(III)

wherein $R^1$ and $R^3$ and n are as described above for compound I.

The invention further provides for 4-thio coumarin derivatives of the formula X

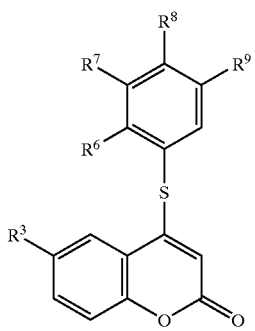

(X)

wherein $R^3$ is as described for the compound of formula I, $R^6$ is selected from halogen, halogenated methyl, methoxy, and ethoxy;

$R^7$ is selected from H, halogen, halogenated methyl, methoxy, and ethoxy;

$R^8$ is selected from H, halogen, halogenated methyl, methoxy, and ethoxy, and $R^9$ is selected from H, halogen, halogenated methyl, methoxy, and ethoxy.

The invention also provides a synthetic process for the preparation of compounds of the formula I. The process uses mild reaction conditions, which provides a high substituent tolerance. Thus, the process is applicable to the preparation of a wide variety of 4-thio substituted coumarin derivatives with diverse substitution patterns. Additionally, the process is appropriate for use with the solid-support (solid phase) synthesis of 4-thio substituted coumarin derivatives. Thus, the process provides a method for producing a library of 4-thio substituted coumarin derivatives for biological screening.

DETAILED DESCRIPTION OF THE PREFERRED EMBODIMENTS

The term "halo" or "halogen" as used herein includes fluorine, chlorine, bromine and iodine.

The term "lower alkyl" as used herein contemplates both straight and branched chain alkyl radicals containing from one to six carbon atoms and includes methyl, ethyl, propyl, isopropyl, butyl, isobutyl, tert-butyl, and the like.

The term "cycloalkyl" as used herein contemplates cyclic alkyl radicals containing form 3 to 7 carbon atoms and includes cyclopropyl, cyclopentyl, cyclohexyl, and the like.

The term "lower alkenyl" as used herein contemplates both straight and branched chain alkene radicals containing from two to six carbon atoms.

The term "lower alkynyl" as used herein contemplates both straight and branched chain alkyne radicals containing from two to six carbon atoms.

The term "$C_2$–$C_8$ acyl" as used herein contemplates both straight and branched chain acyl radicals containing from two to eight carbon atoms and includes acetyl, propionyl, 2-methylbutyryl and the like.

The term "lower alkyl ester" as used herein contemplates the straight and branched chain lower alkyl esters including —$CO_2CH_3$, —$CO_2CH_2CH_3$, —$CO_2CH(CH_3)CH_2CH_3$, and the like.

The term "lower alkyl amide" as used herein contemplates the straight and branched chain lower alkyl amides including

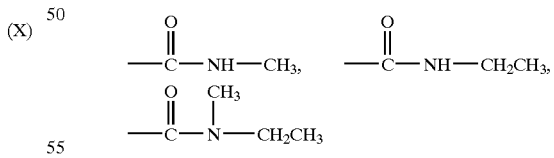

and the like.

The terms "aralkyl" as used herein contemplates a lower alkyl group which has as a substituent an aromatic group.

The term "aromatic group" as used herein contemplates 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aromatic groups having heteroatoms in the ring structure may also be referred to as "aryl heterocycles" or "heteroaromatics". The term aromatic groups also includes polycyclic ring systems having two or more rings in which two carbons are common to two adjoining rings (the rings are "fused") wherein at least one of the rings is aromatic, e.g., the other rings can be cycloalkyls, cycloalkenyls, aryl, heterocycles and/or heteroaryls.

All value ranges, for example those given for n and m, are inclusive over the entire range. Thus, a range between 0–4 would include the values 0, 1, 2, 3 and 4.

One embodiment of the present invention pertains to novel 4-thio-coumarin derivatives of the formula I:

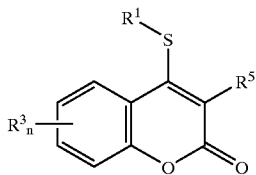

(I)

wherein
$R^1$ is selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_6$ acyl, lower alkyl ester, amide, and lower alkyl amide;
an unsubstituted or substituted alkyl group, wherein the substituted alkyl group may be substituted with one or more halogen, hydroxy, and lower alkoxy; and
an unsubstituted or substituted cycloalkyl group, wherein the substituted cycloalkyl group may be substituted with one or more halogen, hydroxy, and lower alkoxy;
$R^3$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^3$ is a group of the formula

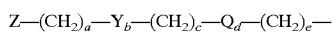

wherein Y and Q are independently selected from an aromatic group, O, S, —CR=CR—,

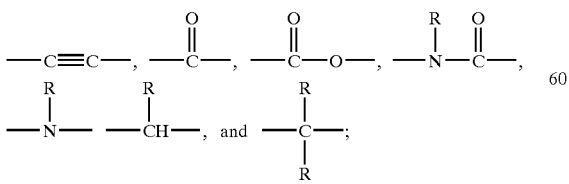

each R is independently selected from H or lower alkyl,

Z is selected from

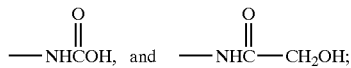

a, c and e are independently selected from values from 0 to 10;
b and d are independently selected from 0 and 1, provided that when a=0 then b=0, and when c=0 then d=0;
or $R^3$ may occupy two adjacent positions to form a fused aromatic ring, n is selected from values between 0 and 4;
$R^5$ is selected from hydrogen, lower alkyl, lower alkenyl, lower alkynyl, and lower aralkyl, each of which may be unsubstituted or substituted with one or more substituents selected from halogen, lower alkyl, and lower alkoxy, thio-lower alkyl, $C_1$–$C_8$ acyl, lower alkyl ester, amide, and lower alkyl amide; or $R^5$ may be a group of the formula

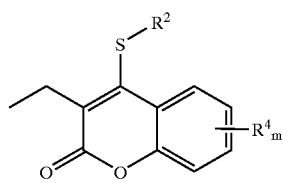

wherein
$R^2$ is selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
an unsubstituted or substituted alkyl group, wherein the substituted alkyl group may be substituted with one or more halogen, hydroxy, and lower alkoxy; and
an unsubstituted or substituted cycloalkyl group, wherein the substituted cycloalkyl group may be substituted with one or more halogen, hydroxy, and lower alkoxy;
$R^4$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^4$ is a group of the formula

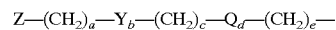

wherein Y and Q are independently selected from an aromatic group, O, S, —CR=CR—,

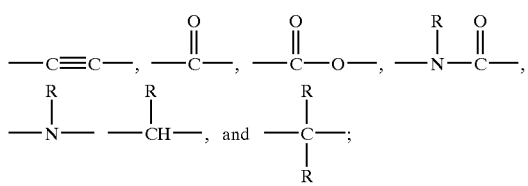

each R is independently selected from H or lower alkyl,

Z is selected from

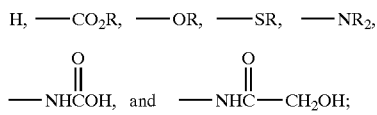

a, c and e are independently selected from values from 0 to 10;

b and d are independently selected from 0 and 1, provided that when a=0 then b=0, and when c=0 then d=0;

or $R^4$ may occupy two adjacent positions to form a fused aromatic ring, and, m is selected from values between 0 and 4.

It is understood that when n is a value greater than 1, each $R^3$ group may be selected independently. Thus, when more than one $R^3$ group is present, the $R^3$ groups may be selected from any of the stated groups so as to be the same or different. This also holds true for $R^4$ when m has a value of greater than 1, and for any other group or substituent which may be selected independently from among various groups or values.

When Y or Q is an ester or amide functionality,

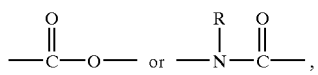

the group may be in either available orientation. Thus, for example, when

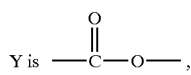

then $R^3$ may be chosen from

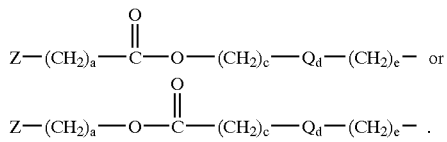

When one or more chiral centers are present in the compounds of the present invention, the individual isomers and mixtures thereof (e.g., racemates, etc.) are intended to be encompassed by the formulae depicted herein.

In one embodiment of the invention, the 3-position of the 4-thio substituted coumarin is unsubstituted ($R^5$ is H) giving a compound of the formula III:

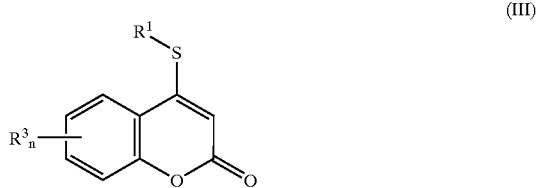

wherein $R^1$, $R^3$ and n are as described above. Table 1 provides representative compounds of the formula III.

TABLE 1

| Comp. No. | $R^1$ | $R^3$ | purity (%) |
|---|---|---|---|
| 9h-B1 | phenyl | 7-OH | 94.7 |
| 9h-B2 | 2-bromophenyl | 7-OH | 94.6 |
| 9h-B3 | 3-bromophenyl | 7-OH | 91.8 |
| 9h-B4 | 4-bromophenyl | 7-OH | >99 |
| 9h-B19 | 3,4-dimethylphenyl | 7-OH | 77.8 |
| 9h-B18 | 3,5-dimethylphenyl | 7-OH | 85.9 |
| 9h-B21 | 2,3-dimethylphenyl | 7-OH | 87.0 |

TABLE 1-continued

[Structure: 4-(R¹S)-coumarin with R³n substituent]

| Comp. No. | R¹ | R³ | purity (%) |
|---|---|---|---|
| 9h-B30 | 3,5-dimethylphenyl | 7-OH | 83.5 |
| 9h-B24 | 2,4-dimethylphenyl | 7-OH | 94.5 |
| 9h-B15 | 2-ethylphenyl | 7-OH | 95.4 |
| 9h-B5 | 2-methylphenyl | 7-OH | 89.2 |
| 9h-B6 | 3-methylphenyl | 7-OH | 83.6 |
| 9h-B8 | 4-methylphenyl | 7-OH | 90.9 |
| 9h-B7 | 2-chlorophenyl | 7-OH | 96.5 |
| 9h-B9 | 3-chlorophenyl | 7-OH | 93.1 |
| 9h-B10 | 4-chlorophenyl | 7-OH | 97.7 |
| 9h-B11 | 2-methoxyphenyl | 7-OH | >99 |
| 9h-B12 | 3-methoxyphenyl | 7-OH | >99 |
| 9h-B13 | 2,4-difluorophenyl | 7-OH | >99 |
| 9h-B14 | 4-methoxyphenyl | 7-OH | 94.3 |
| 9h-B22 | 2-tert-butylphenyl | 7-OH | 88.0 |
| 9h-B27 | 2-naphthyl | 7-OH | 98.2 |
| 9h-B29 | 2,4-dimethoxyphenyl | 7-OH | 95.3 |
| 9h-B23 | 2,4-dichlorophenyl | 7-OH | 94.2 |
| 9h-B26 | 3,4-dichlorophenyl | 7-OH | 93.8 |
| 9h-B17 | 4-fluorophenyl | 7-OH | >99 |

TABLE 1-continued

| Comp. No. | R¹ | R³ | purity (%) |
|---|---|---|---|
| 9h-B31 | 4-tert-butylphenyl | 7-OH | 74.9 |
| 9h-B16 | 3-fluorophenyl | 7-OH | >99 |
| 9h-B20 | 2-fluorophenyl | 7-OH | 97.9 |
| 9h-B28 | 4-(methylthio)phenyl | 7-OH | 94.1 |
| 9h-B25 | 2,6-dichlorophenyl | 7-OH | 97.7 |
| 3a-B5 | 2-methylphenyl | — | 100 |
| 3a-B10 | 4-chlorophenyl | — | 100 |
| 3b-B1 | phenyl | 6-CH₃ | 100 |
| 3b-B5 | 2-methylphenyl | 6-CH₃ | 100 |
| 3b-B10 | 4-chlorophenyl | 6-CH₃ | 100 |
| 3c-B1 | phenyl | 6-Cl | 100 |
| 3d-B1 | phenyl | 7-OCH₃ | 100 |
| 3d-B5 | 2-methylphenyl | 7-OCH₃ | 100 |
| 3d-B10 | 4-chlorophenyl | 7-OCH₃ | 100 |
| 9i-B1 | phenyl | 7-OH, 8-CH₃ | >99 |
| 9i-B2 | 2-bromophenyl | 7-OH, 8-CH₃ | 98.9 |
| 9i-B3 | 3-bromophenyl | 7-OH, 8-CH₃ | >99 |
| 9i-B4 | 4-bromophenyl | 7-OH, 8-CH₃ | >99 |
| 9i-B5 | 2-methylphenyl | 7-OH, 8-CH₃ | 96.9 |
| 9i-B6 | 3-methylphenyl | 7-OH, 8-CH₃ | 97.6 |
| 9i-B7 | 2-chlorophenyl | 7-OH, 8-CH₃ | >99 |
| 9i-B31 | 4-tert-butylphenyl | 7-OH, 8-CH₃ | 84.5 |

TABLE 1-continued

| Comp. No. | R¹ | R³ | purity (%) |
|---|---|---|---|
| 9i-B20 | 2-F, 4-methylphenyl | 7-OH, 8-CH$_3$ | 95.5 |
| 9i-B16 | 3-F, 4-methylphenyl | 7-OH, 8-CH$_3$ | 96.4 |
| 9i-B28 | 4-(CH$_3$S)phenyl | 7-OH, 8-CH$_3$ | >99 |
| 9i-B13 | 2,4-diF, 4-methylphenyl | 7-OH, 8-CH$_3$ | 94.8 |
| 9i-B29 | 2-OCH$_3$, 4-OCH$_3$ phenyl | 7-OH, 8-CH$_3$ | 97.7 |
| 9i-B22 | 2-tert-butylphenyl | 7-OH, 8-CH$_3$ | 72.9 |
| 9i-B27 | 2-naphthyl | 7-OH, 8-CH$_3$ | >99 |
| 9j-B1 | phenyl | 6-OH | 98.4 |
| 9j-B13 | 2,4-diF-phenyl | 6-OH | >99 |
| 9j-B29 | 2-OCH$_3$, 4-OCH$_3$ phenyl | 6-OH | >99 |
| 9j-B22 | 2-tert-butylphenyl | 6-OH | 93.6 |

TABLE 1-continued

| Comp. No. | R¹ | R³ | purity (%) |
|---|---|---|---|
| 904 | 2-F-phenyl | 6-F | >99 |
| 902 | 2,6-diCl-phenyl | 6-F | >99 |
| 901 | 2,5-diCl-phenyl | 6-F | >99 |
| 910 | 2,4-diF-phenyl | 6-F | >99 |
| 894 | 2-Cl-phenyl | 6-F | >99 |
| 899 | 2-Cl, 4-F phenyl | 6-F | >99 |
| 877 | 2-Cl-phenyl | 5,6-fused benzene | >99 |
| 824 | 2-F-phenyl | 6-OCH$_3$ | >99 |
| 830 | 2,4-diF-phenyl | 6-OCH$_3$ | >99 |

In a further embodiment of the invention, the 4-thio substituted coumarin is a compound of the formula X

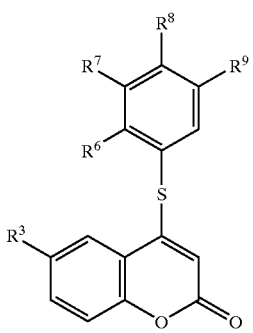

(X)

wherein $R^3$ is as described for the compound of formula I,
$R^6$ is selected from halogen, halogenated methyl, methoxy, and ethoxy;
$R^7$ is selected from H, halogen, halogenated methyl, methoxy, and ethoxy;
$R^8$ is selected from H, halogen, halogenated methyl, methoxy, and ethoxy, and
$R^9$ is selected from H, halogen, halogenated methyl, methoxy, and ethoxy.

In a prefered embodiment for compounds of the formula X, $R^7$ is hydrogen and $R^3$ is selected from halogen and lower alkoxy. In a further prefered embodiment, when $R^3$, $R^6$, $R^7$, or $R^8$ is a halogen, the halogen is preferably fluorine or chlorine.

In another embodiment of the present invention, the 3-position of the 4-thio substituted coumarin is substituted with a group of the formula:

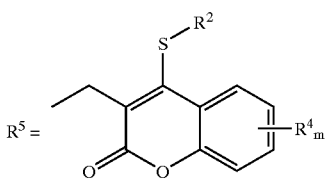

resulting in a symmetric or unsymmetric coumarin dimer having the formula (II):

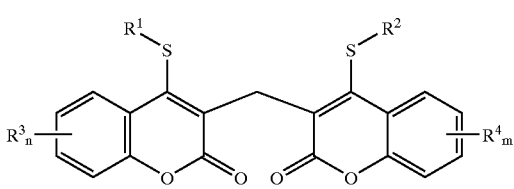

(II)

wherein
$R^1$ and $R^2$ are independently selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
an unsubstituted or substituted alkyl group, wherein the substituted alkyl group is may be substituted with one or more halogen, hydroxy, and lower alkoxy; and
an unsubstituted or substituted cycloalkyl group, wherein the substituted cycloalkyl group may be substituted with one or more halogen, hydroxy, and lower alkoxy;
each $R^3$ and $R^4$ is independently selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or is a group of the formula

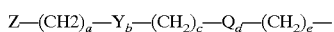

wherein Y and Q are independently selected from an aromatic group, O, S, —CR=CR—,

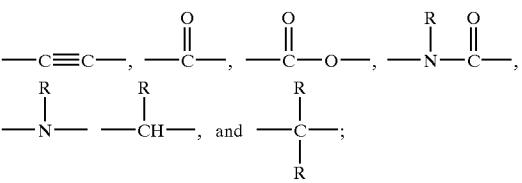

each R is independently selected from H or lower alkyl,
Z is selected from

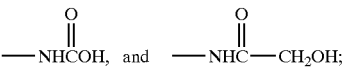

a, c and e are independently selected from values from 0 to 10;
b and d are independently selected from 6 and 1, provided that when a=0 then b=0, and when c=0 then d=0;
or $R^3$ or $R^4$ may occupy two adjacent positions to form a fused aromatic ring, n and m are independently selected from values between 0 and 4.

In one embodiment of the invention, the 5-, 6-, 7-, and 8-positions of the 4-thio substituted coumarin dimers are unsubstituted (n and m are 0) giving a compound of the formula $II_a$:

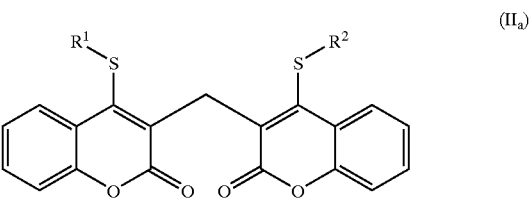

($II_a$)

wherein $R^1$, $R^3$ and are as described above with respect to formula II. Table 2 provides representative compounds of the formula $II_a$.

TABLE 2

Structure: bis-coumarin with R¹S- and R²S- substituents connected by CH₂ bridge

| Comp No. | R¹ | R² | purity |
|---|---|---|---|
| 94-B1 | phenyl | phenyl | 100% |
| 56-C3 | 3,4-dimethylphenyl | 3,4-dimethylphenyl | >99% |
| 56-C3 | 4-methylphenyl | 4-methylphenyl | 100% |
| 56-C4 | 4-chlorophenyl | 4-chlorophenyl | 100% |
| 56-C5 | 2-chloro-4-fluorophenyl | 2-chloro-4-fluorophenyl | 100% |
| 56-C6 | 2-naphthyl | 2-naphthyl | 100% |
| 56-C7A | 2,4-dichlorophenyl | 2,4-dichlorophenyl | 100% |
| 56-C9 | 3,4-dichlorophenyl | 3,4-dichlorophenyl | 100% |
| 56-C10 | 2-fluorophenyl | 2-fluorophenyl | 100% |
| 56-C13 | 4-(methylthio)phenyl | 4-(methylthio)phenyl | 100% |
| 56-C14 | 2-tert-butylphenyl | 2-tert-butylphenyl | 100% |
| 56-C15 | 4-tert-butylphenyl | 4-tert-butylphenyl | 100% |
| 56-C16 | 2,4-difluorophenyl | 2,4-difluorophenyl | 100% |
| 56-C18 | 4-methoxyphenyl | 4-methoxyphenyl | 100% |
| 94-B2 | 2,4-dimethylphenyl | 2,4-dimethylphenyl | 100% |
| 94-B3 | 2,5-dimethylphenyl | 2,5-dimethylphenyl | 100% |
| 94-B4 | 2,6-dimethylphenyl | 2,6-dimethylphenyl | 100% |
| 94-B5 | 2-ethylphenyl | 2-ethylphenyl | 100% |
| 94-B6 | 2-bromophenyl | 2-bromophenyl | 100% |
| 94-B7 | 3-bromophenyl | 3-bromophenyl | 100% |
| 94-B8 | 2-chlorophenyl | 2-chlorophenyl | 100% |

TABLE 2-continued

[Structure: bis(4-thio-coumarin) methylene compound with R¹S- and R²S- substituents]

| Comp No. | R¹ | R² | purity |
|---|---|---|---|
| 94-B9 | 3-Cl-phenyl | 3-Cl-phenyl | 100% |
| 94-B10 | 3-CH₃-phenyl | 3-CH₃-phenyl | 100% |
| 94-B11 | 3-CH₃O-phenyl | 3-CH₃O-phenyl | 100% |
| 94-B12 | 2-OCH₃-phenyl | 2-OCH₃-phenyl | 100% |
| 94-B13 | 2-CH₃-phenyl | 2-CH₃-phenyl | 100% |
| 94-B14 | 4-CH₃O-phenyl | 4-CH₃O-phenyl | 100% |
| 94-B16 | benzyl (PhCH₂) | benzyl (PhCH₂) | 100% |
| 55-A1 | 4-Br-phenyl | phenyl | 100% |
| 55-A2 | 4-Br-phenyl | 2-Br-phenyl | 100% |
| 55-A3 | 4-Br-phenyl | 3-Br-phenyl | 100% |
| 55-A5 | 4-Br-phenyl | 2,4-(CH₃)₂-phenyl | 100% |
| 55-A6 | 4-Br-phenyl | 2,4-(CH₃)₂-phenyl | 100% |
| 55-A7 | 4-Br-phenyl | 2,3-(CH₃)₂-phenyl | 100% |
| 55-A8 | 4-Br-phenyl | 3,5-(CH₃)₂-phenyl | 100% |
| 55-A9 | 4-Br-phenyl | 2,5-(CH₃)₂-phenyl | 100% |
| 55-A10 | 4-Br-phenyl | 2-CH₂CH₃-phenyl | 100% |
| 55-A11 | 4-Br-phenyl | 2-CH₃-phenyl | 100% |
| 55-A12 | 4-Br-phenyl | 3-CH₃-phenyl | 100% |
| 55-A13 | 4-Br-phenyl | 4-CH₃-phenyl | 100% |
| 55-A14 | 4-Br-phenyl | 2-Cl-phenyl | 100% |
| 55-A15 | 4-Br-phenyl | 3-Cl-phenyl | 100% |

TABLE 2-continued

| Comp No. | R¹ | R² | purity |
|---|---|---|---|
| 55-A16 | Br-C6H4- (para) | Cl-C6H4- (para) | 100% |
| 55-A17 | Br-C6H4- (para) | 2-OCH3-C6H4- | 100% |
| 55-A18 | Br-C6H4- (para) | 3-OCH3-C6H4- | 100% |
| 55-A19 | Br-C6H4- (para) | 4-F,2-Cl-C6H3- | 100% |
| 55-A20 | Br-C6H4- (para) | 2-naphthyl | 100% |
| 55-A21 | Br-C6H4- (para) | 2,4-Cl2-C6H3- | 100% |
| 55-A22 | Br-C6H4- (para) | 2,6-Cl2-C6H3- | 100% |
| 55-A23 | Br-C6H4- (para) | 2,3-Cl2-C6H3- | 100% |
| 55-A24 | Br-C6H4- (para) | 2-F-C6H4- | 100% |
| 55-A25 | Br-C6H4- (para) | 3-F-C6H4- | 100% |
| 55-A26 | Br-C6H4- (para) | 4-F-C6H4- | 100% |
| 55-A27 | Br-C6H4- (para) | CH3S-C6H4- (para) | 100% |
| 55-A28 | Br-C6H4- (para) | 2-C(CH3)3-C6H4- | 100% |
| 55-A29 | Br-C6H4- (para) | 4-C(CH3)3-C6H4- | 100% |

In another aspect of the invention, a synthetic process for the preparation of compounds of the formula I is provided. The inventive process uses mild reaction conditions, which provides a high substituent tolerance. The product is obtained in high yield and high purity. The process of the present invention is illustrated by Scheme I:

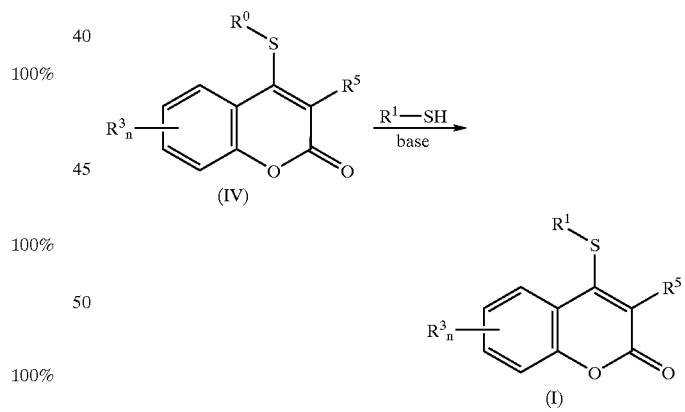

Scheme I wherein $R^1$ is selected from groups that, in combination with the oxygen atom to which it is attached, forms a good leaving group which can be replaced by the thiol nucleophile. $R^0$ is preferably selected from the group consisting of aryl sulfones (tosyl, etc.) triflate, and polyhalogenated aromatic compounds. A tosyl group is particularly preferred. Preparation of compounds of the formula IV is typically from the corresponding alcohol according to procedures know in the art. For example, compounds of the formula IV may be prepared by treating the corresponding 4-hydroxycoumarin with protective group forming agent (non-limiting example includes p-toluenesulfonyl chloride), and a base in a suitable organic solvent. See Wu, J.; Liao, Y.; Yang, Z., *J. Org. Chem.* 2001, 66, 3642. 4-Hydroxycoumarins may be purchased from commercial sources or may be prepared by processes known in the art. For the general method for preparing 4-hydroxycoumarins, see (a) Laurin P.; Ferroud, D.; Klich, M.; Dupuis-Hamelin, C.; Mauvais, P.; Lassaigne, P.; Bonnefoy, A. and Musicki, B., *Bioorg. Med. Chem. Lett.* 1999, 9, 2079–2084. (b) Appendino, G.; Cravotto, G.; Giovenzana, G. B. and Palmisano, G. J., *Nat. Prod.* 1999, 62, 1627–1631.

The base employed in reaction Scheme I may be chosen from amine bases, hydroxide salts (non-limiting examples include sodium hydroxide and tetraalkylamonium hydroxides), carbonate salts, alkoxide salts (non-limiting examples include sodium methoxide and potassium t-butoxide) and the like. Preferred bases are amine bases, and particularly, the tertiary amines, such as triethylamine. The solvent may be chosen from the organic solvents known in the art that are compatible with the reaction conditions, as would be apparent to one of skill in the art. Suitable solvents may include, but are not limited to, methylene chloride, THF, toluene, dialkylethers, ketones (non-limiting examples include acetone and methyl ethyl ketone), esters (a non-limiting example includes ethyl acetate), alcohols (non-limiting examples include methanol and ethanol), acetonitrile, DMSO, DMF, and mixtures thereof. A preferred solvent is methylene chloride.

The reaction is carried out under mild conditions. Preferably, the reaction is run until completion, as monitored by thin-layer chromatography, HPLC or another comparable method. The reaction temperature is preferably less than about 80° C. It is particularly preferred that the reaction be performed at room temperature (about 20–25° C.). Additionally the reaction is capable of being performed under an air atmosphere, although inert atmospheres (e.g., nitrogen, argon, etc.) may also be used. Thus, the inventive process is applicable to the preparation of a wide variety of 4-thio substituted coumarin derivatives with diverse substitution patterns. As a result, the inventive process in appropriate for use with the solid-support (solid phase) synthesis of 4-thio substituted coumarin derivatives. Thus, the inventive process provides a method for producing a library of 4-thio substituted coumarin derivatives for biological screening.

In another embodiment of the present invention, coumarin dimers are prepared from a compound of the formula V according to the reaction Scheme II:

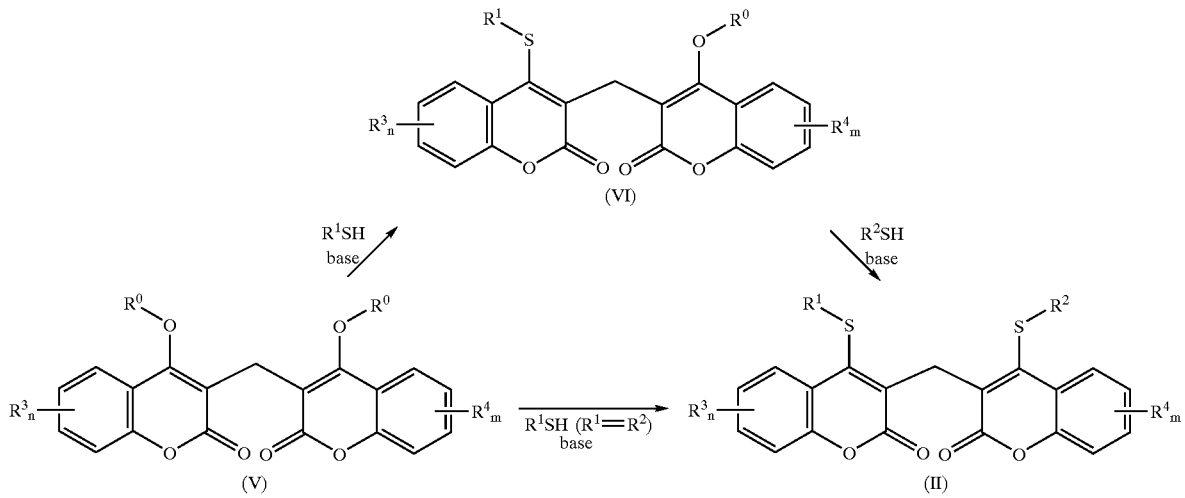

wherein $R^0$, is as defines in Scheme I, and $R^1$, $R^2$, $R^3$, $R^4$, n and m are as defined in Formula II. The compound VI is treated with a thiol, represented by $R^1SH$ and/or $R^2SH$, and a base in an appropriate solvent. The base, solvent and reaction conditions are as described above for Scheme I.

As shown in Scheme II, when $R^1$ is the same as $R^2$, the reaction of the compound of the formula V with a thiol and base to give the product II can be carried out in a single reaction step. In another embodiment of the invention, when $R^1$ is not the same as $R^2$, the substitution may be carried out in two steps. Short reaction times, even in the presence of excess thiol, generally results in the mono-substituted product (VI). Longer reaction times in the presence of two or more equivalents of thiol results in the final product (II).

In one embodiment, a compound linked to a solid support, represented by the formula VII, is treated according to the process of reaction Scheme I with a thiol and a base in an appropriate solvent. The product of the substitution reaction, represented by the formula VIII, is cleaved from the solid support. This embodiment is summarized in reaction Scheme III:

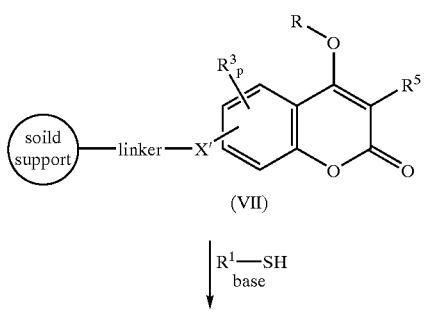

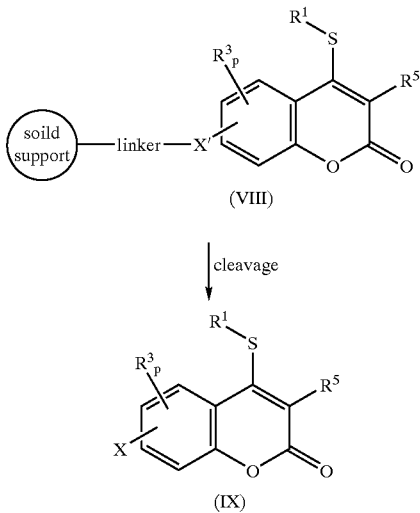

(VIII)

↓ cleavage (IX)

wherein $R^0$ is as defined for Scheme I, and $R^1$, $R^3$ and $R^5$ are as defined above for the compound of Formula I, p is selected from values between 0 and 3.

X' is a selected from O, S, —O—lower alkyl- or a group of the formula $$Z'-(CH_2)_a-Y_b-(CH_2)_c-Q_d-(CH_2)_e-$$

wherein Y and Q are independently selected from an aromatic group, O, S, —CR=CR—,

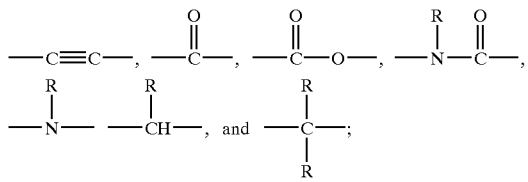

each R is independently selected from H or lower alkyl,

Z' is selected from

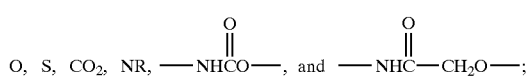

a, c and e are independently selected from values from 0 to 10; and b and d are independently selected from 0 and 1, provided that when a=0 then b=0, and when c=0 then d=0.

X is the chemical group that results from the cleavage of X' and linker. Thus, for example, if X' is O, then X may be HO— after cleavage, and if X' is —O—lower alkyl-, then X may be HO— lower alkyl after cleavage. More generally, when X' is selected from a group of the formula Z'—$(CH_2)_a$—$Y_b$—$(CH_2)_c$—$Q_d$—$(CH_2)_e$—, then X may be a group of the formula HZ'—$(CH_2)_a$—$Y_b$—$(CH_2)_c$—$Q_d$—$(CH_2)_e$—.

The solid support is an insoluble, functionalized, polymeric material to which library members or reagents may be attached via a linker, allowing them to be readily separated (by filtration, centrifugation, etc.) from excess reagents, soluble reaction by-products, or solvents. The solid support is chosen from the solid support materials known in the art, e.g., commercially available resins used for solid phase synthesis in combinatorial chemistry or in solid phase peptide synthesis. For example, the solid support may be chosen from cross-linked polystyrene resins, polystyrene/DVB-polyethylene resins (for example, TentaGel resin, ArgoGel, etc.), controlled-pore glass and Kieselguhr/polyacrylamide. A preferred solid support is a high-capacity polystyrene macrobead.

The linker is a chemical moiety that provides a means of attachment for the immobilized chemical reagent to the solid support. The linker may be any chemical component capable of being selectively cleaved to release a compound of the formula IX from the solid support. Yields for the loading and cleavage to the linker should be as quantitative as possible. The linker may be chosen from those customarily used in the art that are stable to the reactions conditions. Examples of suitable linkers may be found in the review by Guillier et al., *Chem. Rev.* 2000, 100, 2019–2157. Preferred linkers are silyl based linkers, for example the silyl based linkers disclosed in Sternson et al., *J. Am. Chem. Soc.* 2001, 123, 1740–1747, Blackwell et al., *Org. Lett.* 2001, 3, 1185–1188, Pelish et al., *J. Am. Chem. Soc.* 2001, 123, 6740–6741, and Tallarico et al., *J. Comb. Chem.* 2001, 3, 312–318, and the like.

A preferred method of generating a 4-thio substituted coumarin library using the process of the present invention is to employ silyl linker-based high capacity macrobeads as a solid support in order to realize a "one bead, one compound" concept. These beads have a high-capacity (up to about 4 mmol/g) and provide sufficient material from a single bead for multiple assays. The silyl linker allows compounds generated on the beads to be released utilizing volatile cleavage reagents (such as HF/pyridine or trimethylsilyl-methanol) so that the compounds can go directly into biological assays without further purification. The purity of the products, as determined by LC-MS, is very high, often exceeding 90%, and in some cases >99% purity was obtained.

It may be advantageous to employ a temporary protecting group in achieving the final product. The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

The compounds and processes disclosed herein are useful in the production of a library of 4-thio substituted coumarin derivatives for biological screening. Derivatives of coumarin posses a range of biological activities. Coumarin-based compounds have shown efficacy, for example, as anticoagulants, antifungals, and antivirals.

EXAMPLES

In the illustrative examples set forth herein, the following general methods, apparatus and material may be employed. It should be noted that when purities of 100% are reported, the products are pure to the limit of detection for the analysis used.

Materials: Reaction solvents were commercially purchased from Acros and Aldrich without further purification and reagents were used as received. Flash column chromatography was performed on Merck Silica Gel 60 (230–400 mesh) using reagent grade hexanes, dichloromethane, methanol and ethyl acetate.

Process for the Preparation of Dicumarol Starting Materials

The representative process described below in Scheme IV may be expanded for use in preparing a wide variety of dicumarol derivatives. See Appendino, G.; Cravotto, G.; Giovenzana, G. B. and Palmisano, G. J., *Nat. Prod.* 1999, 62, 1627–1631.

evaporated and the residue was purified by flash chromatography (silica gel) to afford the corresponding product C.

From D to E:

To a solution of compound D (1.0 eq.) and imidazole (1.1 eq.) in dichloromethane, tert-butyldimethylsilyl chloride (1.1 eq.) was added at room temperature. After the reaction was completed, the mixture was filtered and the filtrate was evaporated and the residue was purified by flash chromatography (silica gel) to afford the corresponding product E.

From C, E to F:

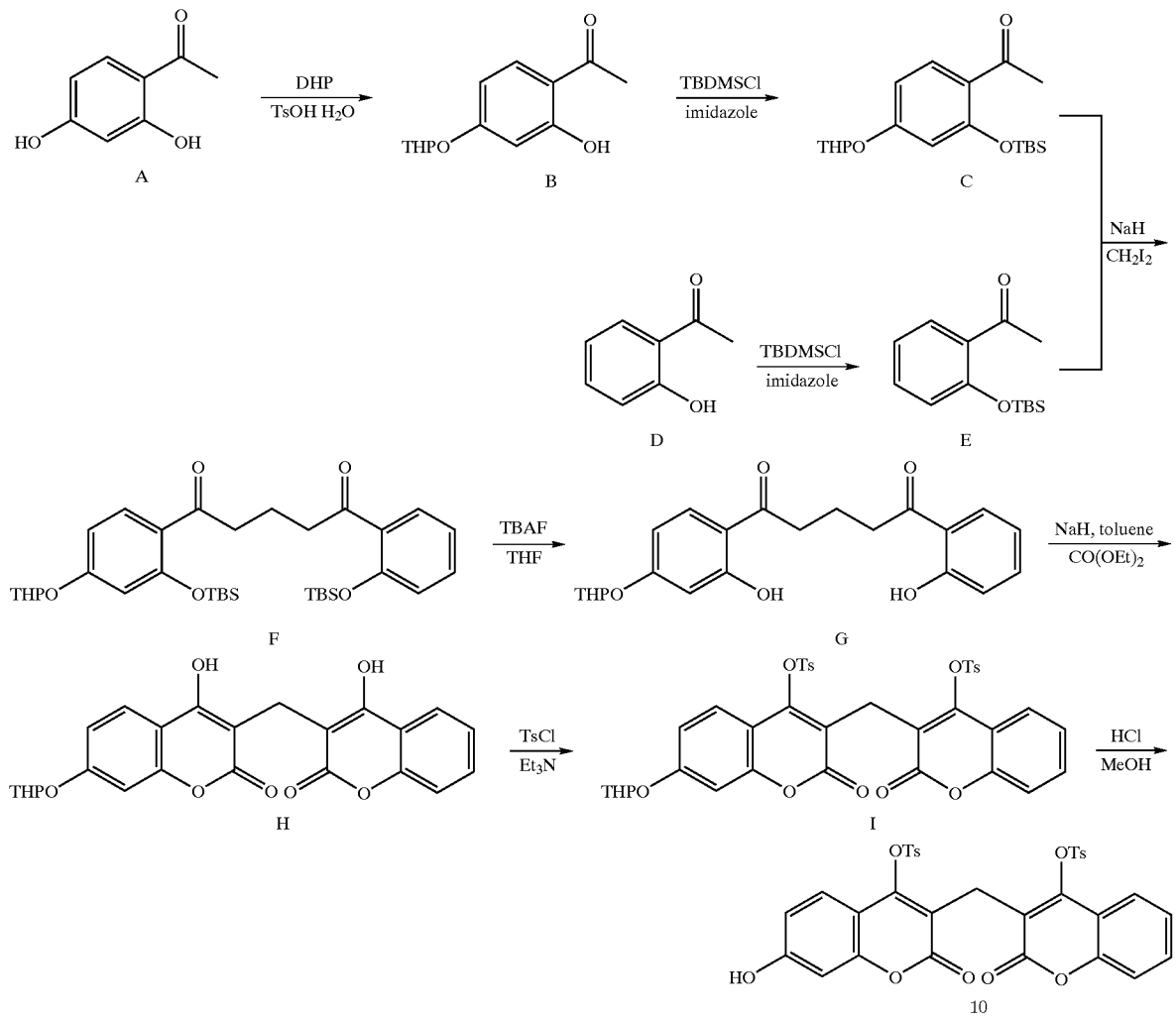

Scheme IV

Synthetic Procedure:

From A to B:

To a solution of compound A (1.0 eq.) and TsOH.H$_2$O (cat.) in ether, 3,4-dihydroxy-2H-pyran (DHP) (5.0 eq.) was added at room temperature. After the reaction was completed, the mixture was evaporated and the residue was purified by flash chromatography (silica gel) to afford the corresponding product B.

From B to C:

To a solution of compound B (1.0 eq.) and imidazole (1.1 eq.) in dichloromethane, tert-butyldimethylsilyl chloride (1.1 eq.) was added at room temperature. After the reaction was completed, the mixture was filtered and the filtrate was To a solution of compound C (1.0 eq.), E (1.0 eq) and sodium hydride (2.4 eq.) in toluene, diiodomethane (1.1 eq.) was added at room temperature. The reaction was stirred under reflux. After the reaction was completed, the mixture was filtered and the filtrate was evaporated and the residue was purified by flash chromatography (silica gel) to afford the corresponding product F.

From F to G:

To a solution of compound F (1.0 eq.) in THF, tetrabutylammonium fluoride (1.0 M in THF) (1.2 eq) was added at room temperature. After the reaction was completed, the mixture was evaporated and the residue was purified by flash chromatography (silica gel) to afford the corresponding product G.

From G to H:

To a solution of compound G (1.0 eq.) and sodium hydride (2.4 eq.) in toluene, CO(OEt)$_2$ (1.2 eq.) was added at room temperature. The reaction was stirred under reflux overnight. After the reaction was completed, the mixture was washed with water. The inorganic phase was separated and evaporated. The compound H was obtained as solid and directly used in the next step without further purification.

From H to I.

To a solution of compound H (1.0 eq.) and p-toluenesulfonyl chloride (1.1 eq.) in dichloromethane, triethylamine (1.5 eq.) was added at room temperature. After the reaction was completed, the mixture was filtered and the filtrate was evaporated. The residue was purified by flash chromatography (silica gel) to afford the corresponding product I.

From I to 10:

To a solution of compound I (1.0 eq.) in methanol, HCl (3.0 M in water) was added at room temperature. After the reaction was completed, the mixture was separated and extracted with ethyl acetate. The organic phase was combined and washed with brine. After dried in Na2SO$_4$, the solvent was removed and the residue was purified by flash chromatography (silica gel) to afford the corresponding product 10.

$^1$H (300M Hz, CDCl$_3$): δ 2.40 (s, 6H), 2.65 (s, 2H), 6.70 (m, 2H), 7.20–7.60 (m, 9 H), 7.70 –7.80 (m, 4H), 10.10 (s, 1H).

Example 1

To a solution of dicumarol (10 mmol) and p-toluenesulfonyl chloride (1.0 eq.) in dichloromethane (20 ml), triethylamine was added at room temperature under air atmosphere. After the reaction was complete, as monitored by TLC, the reaction mixture was evaporated and the residue was purified by flash chromatography (silica gel) to afford the product, 3,3'-methylenebis[4-tosylcoumarin].

Example 2

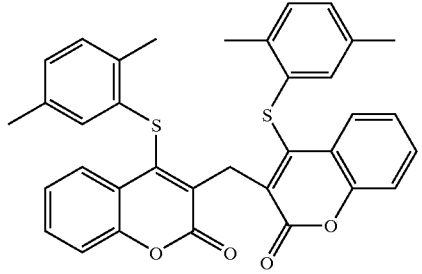

C$_{35}$H$_{28}$O$_4$S$_2$
Exact Mass: 576.14
Mol. Wt.: 576.73

Compound 56-C3

To a solution of 3,3'-methylenebis[4-tosylcoumarin] (1.0 mmol) and 2,5-dimethylbenzenethiol (2.0 eq.) in dichloromethane (5mL), triethylamine (3.0 eq.) was added at room temperature under air atmosphere. After the reaction was complete as monitored by thin-layer chromatography (TLC), the mixture was evaporated and the residue was purified by flash chromatography (silica gel) to afford the corresponding product 56-C3. >99% yield, 100% pure.

$^1$H NMR (500 MHz/CDCl$_3$): δ (ppm): 2.07 (s, 6H), 2.39 (s, 6H), 4.56 (s, 2H), 6.48 (s, 2H), 6.68 (d, J=7.5 Hz, 2H), 6.89 (d, J=7.5 Hz, 2H), 7.09–7.12 (m, 2H), 7.26 (d, J=5.5 Hz, 2H), 7.39–7.41 (m, 2H), 7.68 (dd, J=8.5, 1.5 Hz, 2H).

Example 3

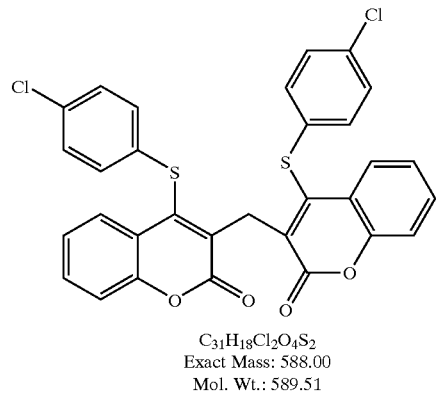

C$_{31}$H$_{18}$Cl$_2$O$_4$S$_2$
Exact Mass: 588.00
Mol. Wt.: 589.51

Compound 56-C4

To a solution of 3,3'-methylenebis[4-tosylcoumarin] (1.0 mmol) and 4-chlorobenzenethiol (2.0 eq.) in dichloromethane (5 mL), triethylamine (3.0 eq.) was added at room temperature under air atmosphere. After the reaction was complete as monitored by TLC, the mixture was evaporated and the residue was purified by flash chromatography (silica gel) to afford the corresponding product 56-C4. >99% yield, 100% pure.

$^1$H NMR (500 MHz/CDCl$_3$): δ (ppm): 4.69 (s, 2H), 7.06 (d, J=6.0 Hz, 4H), 7.07–7.13 (m, 4H), 7.27–7.29 (m, 4H), 7.43–7.45 (m, 2H), 7.73 (dd, J=8.5, 1.5 Hz, 2H).

Example 4

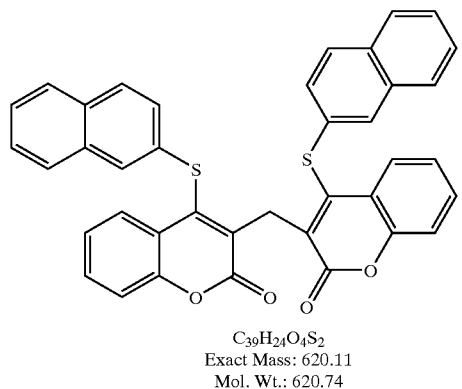

C$_{39}$H$_{24}$O$_4$S$_2$
Exact Mass: 620.11
Mol. Wt.: 620.74

Compound 56-C6

To a solution of 3,3'-methylenebis[4-tosylcoumarin] (1.0 mmol) and 2-naphthylenethiol (2.0 eq.) in dichloromethane (5 mL), triethylamine (3.0 eq.) was added at room temperature under air atmosphere. After the reaction was complete as monitored by TLC, the mixture was evaporated and the residue was purified by flash chromatography (silica gel) to afford the corresponding product 56-C6. >99% yield, 100% pure.

$^1$H NMR (500 MHz/CDCl$_3$): δ (ppm): 4.76 (s, 2H), 6.98 (t, 2H), 7.15–7.19 (m, 4H), 7.26–7.42 (m, 6H), 7.51 (d, J=1.5 Hz, 2H), 7.56–7.75 (m, 6H), 7.76 (d, J=1.5 Hz, 2H).

Example 5

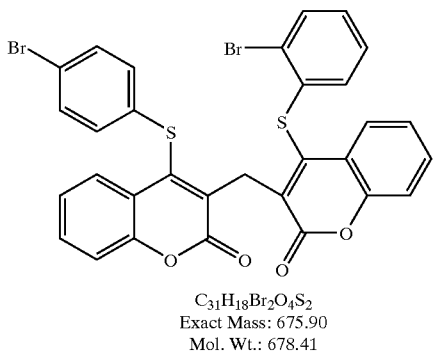

C$_{31}$H$_{18}$Br$_2$O$_4$S$_2$
Exact Mass: 675.90
Mol. Wt.: 678.41

Compound 55-A2

To a solution of 3,3'-methylenebis[4-tosylcoumarin] (1.0 mmol) and 4-bromobenzenethiol (1.0 eq.) in dichloromethane (5 mL), triethylamine (1.5 eq.) was added at room temperature under air atmosphere. After the reaction was complete as monitored by TLC, the mixture was evaporated and the residue was purified by flash chromatography (silica gel) to afford the corresponding product. To a solution of the product 2-bromobenzenethiol (1.0 eq.) in dichloromethane (5 mL), triethylamine (1.5 eq.) was added at room temperature under air atmosphere. After the reaction was complete as monitored by TLC, the mixture was evaporated and the residue was purified by flash chromatography (silica gel) to afford the corresponding product 55-A2. >99% yield, 100% pure.

$^1$H NMR (500 MHz/CDCl$_3$): δ (ppm): 4.66 (s, 2H), 6.70–6.75 (m, 1H), 6.80–6.90 (m, 1H), 6.90–7.02 (m, 2H), 7.14–7.17 (m, 2H), 7.25–7.32 (m, 4H), 7.38–7.47 (m, 4H), 7.69–7.78 (m, 2H).

Example 6

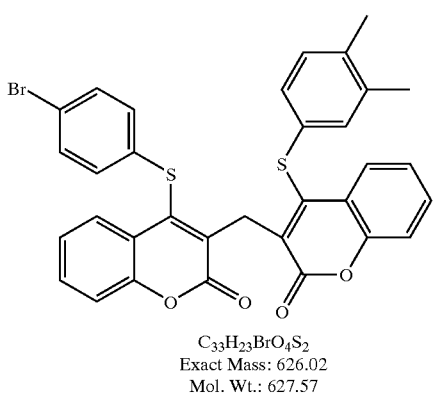

C$_{33}$H$_{23}$BrO$_4$S$_2$
Exact Mass: 626.02
Mol. Wt.: 627.57

Compound 55-A5

To a solution of 3,3'-methylenebis[4-tosylcoumarin] (1.0 mmol) and 4-bromobenzenethiol (1.0 eq.) in dichloromethane (5 mL), triethylamine (1.5 eq.) was added at room temperature under air atmosphere. After the reaction was complete as monitored by TLC, the mixture was evaporated and the residue was purified by flash chromatography (silica gel) to afford the corresponding product. To a solution of the product and 3,4-dimethylbenzenethiol (1.0 eq.) in dichloromethane (5 mL), triethylamine (1.5 eq.) was added at room temperature under air atmosphere. After the reaction was complete as monitored by TLC, the mixture was evaporated and the residue was purified by flash chromatography (silica gel) to afford the corresponding product 55-A5.

Example 7

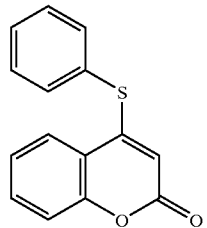

Compound 3a-B1

Benzenethiol (0.30 mmol, 1.2 equiv.) was added to a solution of 4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-B1. 99% yield as colorless oil. 100% pure.

$^1$H NMR (500 MHz, CDCl$_3$) δ (ppm) 5.67 (s, 1H), 7.33–7.38 (m, 2H), 7.50–7.63 (m, 6H), 7.88 (d, J=8.0 Hz, 1H). $^{13}$C NMR (125.7 MHz) δ (ppm) 159.79, 158.17, 152.50, 136.38, 132.57, 131.16, 130.69, 126.45, 124.41, 123.95, 118.08, 117.47, 108.64. MS (APCI) [C$_{15}$H$_{10}$O$_2$S], m/z (M$^+$+1): calcd 255, found 255.

Example 8

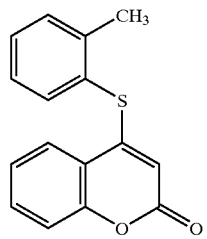

Compound 3a-B5

2-methylbenzenethiol (0.30 mmol, 1.2 equiv.) was added to a solution of 4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-B5. 97% yield as colorless oil. 100% pure.

$^1$H NMR (500 MHz, CDCl$_3$) δ (ppm) 2.45 (s, 3H), 5.52 (s, 1H), 7.31–7.50 (m, 5H), 7.57–7.63 (m, 2H), 7.92 (d, J=8.0 Hz, 1H). $^{13}$C NMR (125.7 MHz) δ (ppm) 159.79, 157.06, 152.58, 143.70, 137.44, 132.52, 131.97, 131.75, 128.12, 125.62, 124.41, 124.13, 118.15, 117.46, 107.87, 20.73. MS (APCI) [C$_{16}$H$_{12}$O$_2$S], M/Z (M$^+$+1): calcd 269, found 269.

Example 9

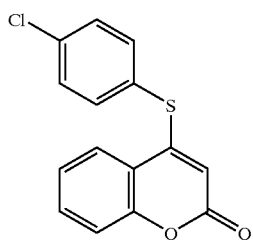

Compound 3a-B10

4-chlorobenzenethiol (0.30 mmol, 1.2 equiv.) was added to a solution of 4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-B10. 98% yield as colorless oil. 100% pure.

$^1$H NMR (500 MHz, CDCl$_3$) δ (ppm) 5.63 (s, 1H), 7.31–7.38 (m, 2H), 7.48–7.62 (m, 5H) 7.83 (d, J=8.0 Hz, 1H). $^{13}$C NMR (125.7 MHz) δ (ppm) 159.55, 157.52, 152.48, 137.89, 137.58, 132.73, 131.00, 124.88, 124.49, 123.88, 117.87, 117.49, 108.78. MS (APCI) [C$_{15}$H$_9$ClO$_2$S], m/z (M$^+$+1): calcd 289, found 289.

Example 10

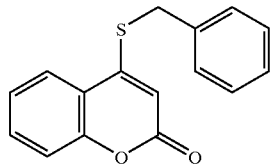

Compound 3a-C7

1-Benzylthiol (0.30 mmol, 1.2 equiv.) was added to a solution of 4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-C7. 57% yield as colorless oil. 100% pure.

$^1$H NMR (500 MHz, CDCl$_3$) δ (ppm) 4.28 (s, 2H), 6.25 (s, 1H), 7.25–7.47 (m, 7H), 7.56 (t, J=8.0, 7.0Hz, 1H), 7.74 (d, J=8.0 Hz, 1H). $^{13}$C NMR (125.7 MHz) δ (ppm) 159.45, 156.31, 152.42, 133.97, 132.45, 129.31, 129.23, 128.50, 124.36, 124.03, 118.23, 117.49, 107.62, 36.02. MS (APCI) [C$_{16}$H$_{12}$O$_2$S], m/z (M$^+$+1): calcd 269, found 269.

Example 11

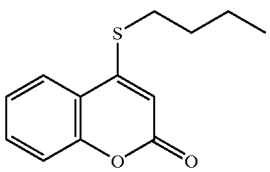

Compound 3a-C10

1-Butanethiol (0.30 mmol, 1.2 equiv.) was added to a solution of 4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-C10. 68% yield as colorless oil. 100% pure.

$^1$H NMR (500 MHz, CDCl$_3$) δ (ppm) 1.00 (t, J=7.5 Hz, 3H), 1.50–1.60 (m, 2H), 1.75–1.85 (m, 2H), 3.03 (t, J=7.5 Hz, 2H), 6.16 (s, 1H), 7.26–7.50 (m, 2H), 7.55 (dt, J=8.5, 1.5 Hz, 1H), 7.76 (dd, J=8.0, 1.5 Hz, 1H). $^{13}$C NMR (125.7 MHz) δ (ppm) 159.64, 156.98, 152.38, 132.33, 124.29, 124.11, 118.50, 117.44, 106.94, 30.80, 29.90, 22.40, 13.79. MS(APCI) [C$_{13}$H$_{14}$O$_2$S], m/z (M$^+$+1): calcd 235, found 235.

Example 12

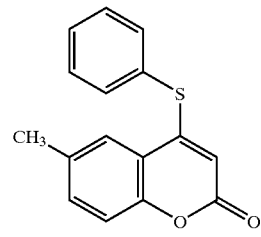

Compound 3b-B1

Benzenethiol (0.30 mmol, 1.2 equiv.) was added to a solution of 6-methyl-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-B1. 94% yield as colorless oil. 100% pure.

$^1$H NMR (500 MHz, CDCl$_3$) δ (ppm) 2.48 (s, 3H), 5.64 (s, 1H), 7.25 (d, J=8.0 Hz, 1H), 7.40 (dd, J=8.5, 1.5 Hz, 1H), 7.50–7.65 (m, 6H). $^{13}$C NMR (125.7 MHz) δ (ppm) 160.03, 158.00, 150.58, 136.39, 134.18, 133.58, 131.11, 130.66, 126.57, 123.70, 117.74, 117.17, 108.54, 21.20. MS (APCI) [C$_{16}$H$_{12}$O$_2$S], m/z (M$^+$+1): calcd 269, found 269.

Example 13

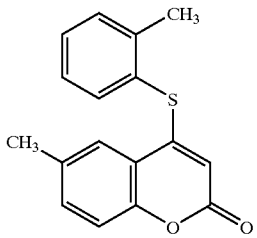

Compound 3b-B5

2-Methylbenzenethiol (0.30 mmol, 1.2 equiv.) was added to a solution of 6-methyl-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-B5. 99% yield as colorless oil. 100% pure.

$^1$H NMR (500 MHz, CDCl$_3$) δ (ppm) 2.44 (s, 3H), 2.48 (s, 3H), 5.49 (s, 1H), 7.24–7.50 (m, 5H), 7.58 (d, J=7.5 Hz, 1H), 7.69 (s, 1H). $^{13}$C NMR (125.7 MHz) δ (ppm) 160.03, 156.89, 150.67, 143.69, 137.46, 134.18, 133.52, 131.95, 131.70, 128.10, 125.74, 123.89, 117.81, 117.18, 107.78, 21.20, 20.73. MS (APCI) [C$_{17}$H$_{14}$O$_2$S], m/Z (M$^+$+1): calcd 283, found 283.

Example 14

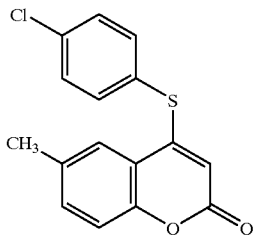

Compound 3a-B10

4-Chloro-benzenethiol (0.30 mmol, 1.2 equiv.) was added to a solution of 6-methyl-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-B10. 97% yield as colorless oil. 100% pure.

$^1$H NMR (500 MHz, CDCl$_3$) δ (ppm) 2.47 (s, 3H), 5.61 (s, 1H), 7.22–7.28 (m, 1H), 7.37–7.42 (m, 1H), 7.49–7.64 (m, 5H). $^{13}$C NMR (125.7 MHz) δ (ppm) 159.80, 157.37, 150.58, 137.85, 137.60, 134.27, 133.73, 130.97, 125.00, 123.63, 117.55, 117.21, 108.69, 21.20. MS (APCI) [C$_{16}$H$_{11}$ClO$_2$S], m/z (M$^+$+1): calcd 303, found 303.

Example 15

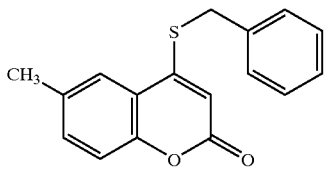

Compound 3a-C7

Benzylthiol (0.30 mmol, 1.2 equiv.) was added to a solution of 6-methyl-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-C7. 64% yield as colorless oil. 100% pure.

$^1$H NMR (500 MHz, CDCl$_3$) δ (ppm) 2.40 (s, 3H), 4.26 (s, 2H), 6.22 (s, 1H), 7.22 (d, J=8.0 Hz, 1H), 7.33–7.47 (m, 6H), 7.51 (s, 1H). $^{13}$C NMR (125.7 MHz) δ (ppm) 159.69, 156.15, 150.51, 134.10, 134.03, 133.43, 129.30, 129.24, 128.48, 123.82, 117.88, 117.19, 107.51, 36.00, 21.13. MS (APCI) [C$_{17}$H$_{14}$O$_2$S], m/z (M$^+$+1): calcd 283, found 283.

Example 16

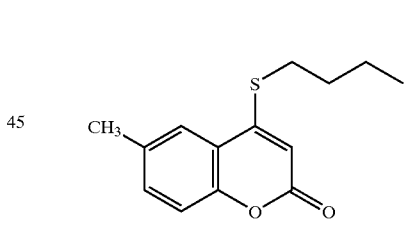

Compound 3a-C10

1-Butanethiol (0.30 mmol, 1.2 equiv.) was added to a solution of 6-methyl-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-C10. 63% yield as colorless oil. 100% pure.

$^1$H NMR (500 MHz, CDCl$_3$) δ (ppm) 1.00 (dt, J=7.0, 2.0 Hz, 3H), 1.52–1.60 (m, 2H), 1.76–1.86 (m, 2H), 2.42 (s, 3H), 3.02 (dt, J=7.0, 2.0 Hz, 2H), 6.14 (s, 1H), 7.22 (dd, J=8.5, 2.0 Hz, 1H), 7.34 (d, J=8.5 Hz, 1H), 7.53 (s, 1H). $^{13}$C NMR (125.7 MHz) δ (ppm) 159.89, 156.81, 150.47, 134.02, 133.33, 123.88, 118.15, 117.15, 106.87, 30.78, 29.90, 22.39, 21.15, 13.79. MS (APCI) [$C_{14}H_{16}O_2S$], m/z (M$^+$+1): calcd 249, found 249.

Example 17

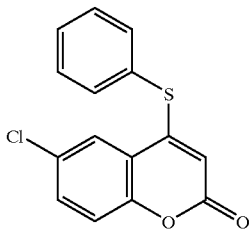

Compound 3c-B1

Benzenethiol (0.30 mmol, 1.2 equiv.) was added to a solution of 6-chloro-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3c-B1. 96% yield as colorless oil. 100% pure.

$^1$H NMR (500 MHz, CDCl$_3$) δ (ppm) 5.68 (s, 1H), 7.30 (d, J=8.5 Hz, 1H), 7.52–7.62 (m, 6H), 7.84 (d, J=2.5 Hz, 1H). $^{13}$C NMR (125.7 MHz) δ (ppm) 159.11, 157.07, 150.94, 136.35, 132.51, 131.37, 130.81, 129.92, 125.96, 123.61, 119.14, 118.85, 109.39. MS (APCI) [$C_{15}H_9ClO_2S$], m/Z (M$^+$+1): calcd 289, found 289.

Example 18

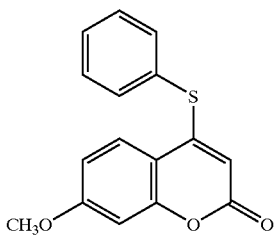

Compound 3d-B1

Benzenethiol (0.30 mmol, 1.2 equiv.) was added to a solution of 7-methoxy-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3d-B1. 99% yield as colorless oil. 100% pure.

$^1$H NMR (500 MHz, CDCl$_3$) δ (ppm) 3.90 (s, 3H), 5.51 (s, 1H), 6.82 (d, J=2.5 Hz, 1H), 6.90 (dd, J=9.0, 2.5 Hz, 1H), 7.49–7.60 (m, 3H), 7.60 (dd, J=7.5, 1.5 Hz, 2H), 7.75 (d, J=9.0 Hz, 1H). $^{13}$C NMR (125.7 MHz) δ (ppm) 163.33, 160.20, 158.17, 154.33, 136.38, 131.03, 130.58, 126.59, 124.99, 112.57, 111.62, 105.65, 101.04, 56.05. MS (APCI) [$C_{16}H_{12}O_3S$], m/z (M$^+$+1): calcd 285, found 285.

Example 19

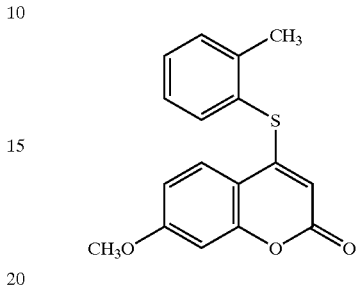

Compound 3d-B5

2-methylbenzenethiol (0.30 mmol, 1.2 equiv.) was added to a solution of 7-methoxy-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3d-B5. 95% yield as colorless oil. 100% pure.

$^1$H NMR (500 MHz, CDCl$_3$) δ (ppm) 2.43 (s, 3H), 3.90 (s, 3H), 5.36 (s, 1H), 6.82 (d, J=2.5 Hz, 1H), 6.90 (dd, J=8.5, 2.5 Hz, 1H), 7.29–7.34 (m, 1H), 7.39–7.48 (m, 2H), 7.57 (d, J=7.5 Hz, 1H), 7.79 (d, J=9.0 Hz, 1H). $^{13}$C NMR (125.7 MHz) δ (ppm) 163.30, 160.22, 157.12, 154.42, 143.70, 137.46, 131.89, 131.64, 128.01, 125.77, 125.15, 112.58, 111.70, 104.89, 101.06, 56.07, 20.75. MS (APCI) [$C_{17}H_{14}O_3S$], m/Z (M$^+$+1): calcd 299, found 299.

Example 20

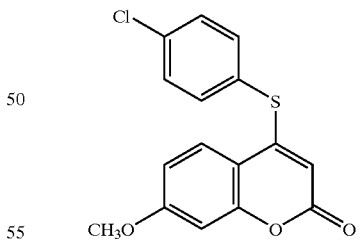

Compound 3d-B10

4-Chlorobenzenethiol (0.30 mmol, 1.2 equiv.) was added to a solution of 7-methoxy-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3d-B 10. 96% yield as colorless oil. 100% pure.

$^1$H NMR (500 MHz, CDCl$_3$) δ (ppm) 3.89 (s, 3H), 5.47 (s, 1H), 6.81 (d, J=2.0 Hz, 1H), 6.89 (dd, J=9.0, 2.5 Hz, 1H), 7.47–7.54 (m, 4H), 7.70 (d, J=9.0 Hz, 1H). $^{13}$C NMR (125.7 MHz) δ (ppm) 163.44, 159.98, 157.51, 154.35, 137.75, 137.57, 130.88, 125.05, 124.91, 112.65, 111.42, 105.78, 101.07, 56.08. MS (APCI) [C$_{16}$H$_{11}$ClO$_3$S], m/z (M$^+$+1): calcd 319, found 319.

Example 21

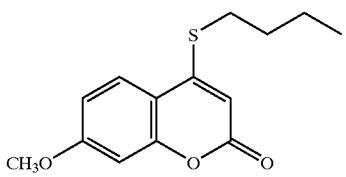

Compound 3d-C10

Butanethiol (0.30 mmol, 1.2 equiv.) was added to a solution of 7-methoxy-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3d-C10. 60% yield as colorless oil. 100% pure.

$^1$H NMR (500 MHz, CDCl$_3$) δ (ppm) 1.00 (t, J=7.5 Hz, 3H), 1.51–1.57 (m, 2H), 1.76–1.82 (m, 2H), 3.01 (t, J=7.5 Hz, 2H), 3.88 (s, 3H), 6.02 (s, 1H), 6.80 (d, J=2.5 Hz, 1H) 6.84 (dd, J=9.0, 2.5 Hz, 1H), 7.64 (d, J=8.5 Hz, 1H). $^{13}$C NMR (125.7 MHz) δ (ppm) 163.15, 160.08, 157.07, 154.20, 125.15, 112.48, 112.07, 104.02, 100.99, 56.01, 30.72, 30.01, 22.39, 13.79. MS (APCI) [C$_{14}$H$_{16}$O$_3$S], M/z (M$^+$+1): calcd 265, found 265.

Example 22

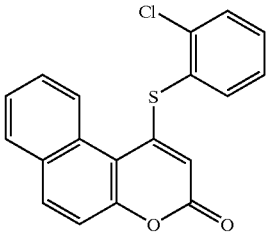

Compound 877

2-Chlorobenzenethiol (0.30 mmol, 1.2 equiv.) was added to a solution of 4-(p-toluenesulfonyloxy)-naphtho[1,2-e]pyran-2-one (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product Compound No. 877. Purity>99

$^1$H NMR: 5.43 (s, 1H), 7.60–7.75 (m, 4H), 7.80–7.85 (m, 2H), 7.92 (dd, J=8.0, 1.5 Hz, 1H), 8.14 (d, J=8.0 Hz, 1H), 8.30 (d, J=9.0 Hz, 1H), 9.08 (d, J=8.5 Hz, 1H). MS (MH+): C$_{19}$H$_{11}$ClO$_2$S, Cal: 339; Found: 339.

Example 23

Scheme VI

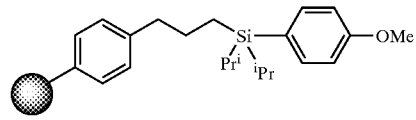

6

1) TMSCl, imidazole
   RT, DCM, 2 h
2) TfOH, DCM, RT, 1.5 h
3) 2,6-lutidine, DCM
   RT, 4 h, 10

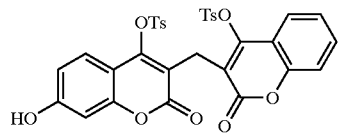

10

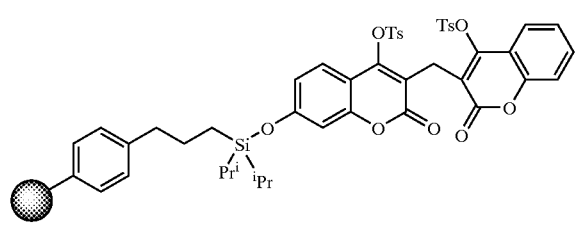

11

ArSH(B1-31)
TEA, DCM
RT, 6 h

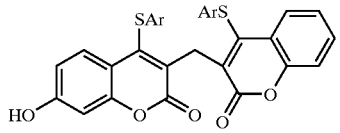

-continued

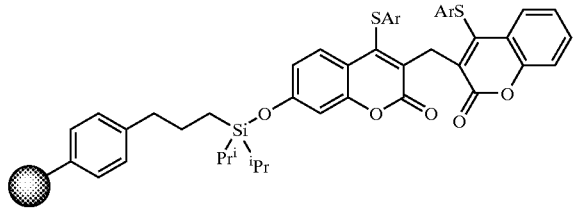

Loading of Hydroxycoumarin 10 onto Resin 6

Silicon-functionalized resin 6 that had been dried under high vacuum for 12 hours was weighed (200 mg) into a 10 mL polypropylene PD-10 column fitted with a Teflon stopcock and swollen in a solution of trimethylsilyl chloride (0.1 mL) and imidazole (20 mg) in $CH_2Cl_2$ (4 mL) under $N_2$ atmosphere for 2 h. The solvent was then drained under positive $N_2$ pressure, and 0.2 mL of trifluoromethanesulfonic acid in $CH_2Cl_2$ (4 mL) was added by syringe. The resin turned red/orange upon acid treatment and was then gently agitated for 1.5 h while still under $N_2$ atmosphere. Once activation was completed, two $CH_2Cl_2$ washes removed excess acid. Then, 10 (2 equiv.) in 2,6-lutidine (0.8 mL) was added and the mixture resulted in a colorless resin. The beads are then gently agitated for an additional 4 hours under $N_2$ atmosphere. The beads were drained, exposed to atmosphere, and subjected to the following wash protocol: $CH_2Cl_2$ (5 mL, 2 h), DMF (5 mL, 2 h), MeOH (5 mL, 2 h), DMF (5 mL, 2 h), and $CH_2Cl_2$ (5 mL, 2 h). The resin 11 was air-dried for 3 h and then placed under high vacuum for 24 h to remove trace solvent and water.

Reaction of Thiols With Resin 11

To a suspension of 11 (20 beads) with thiol (2.5 eq.) in dichloromethane (2 mL), triethylamine (3.0 eq.) was added at room temperature under air atmosphere. The beads are then gently agitated for an additional 6 hours under $N_2$ atmosphere. The beads were drained, exposed to atmosphere, and subjected to the following wash protocol: $CH_2Cl_2$ (2 mL, 2 h), DMF (2 mL, 2 h), MeOH (2 mL, 2 h), DMF (2 mL, 2 h), and $CH_2Cl_2$ (2 mL, 2 h). The resin 12 was then placed under high vacuum for 24 h to remove trace solvent and water.

Cleavage of 12 From Resin

Vacuum-dried resin 12 was transferred into a solvent-resistant scintillation vial and 200 μL of THF and 10 μL of HF/pyridine solution were added. The vial was sealed and agitated for 1 h, at which time 20 μL of methoxytrimethylsilane was added to quench unreacted HF. The beads are further agitated for 30 min to ensure complete quenching. The solution was removed and the beads washed twice. All solvents were combined and concentrated in vacuo to afford the final product 13.

Example 24

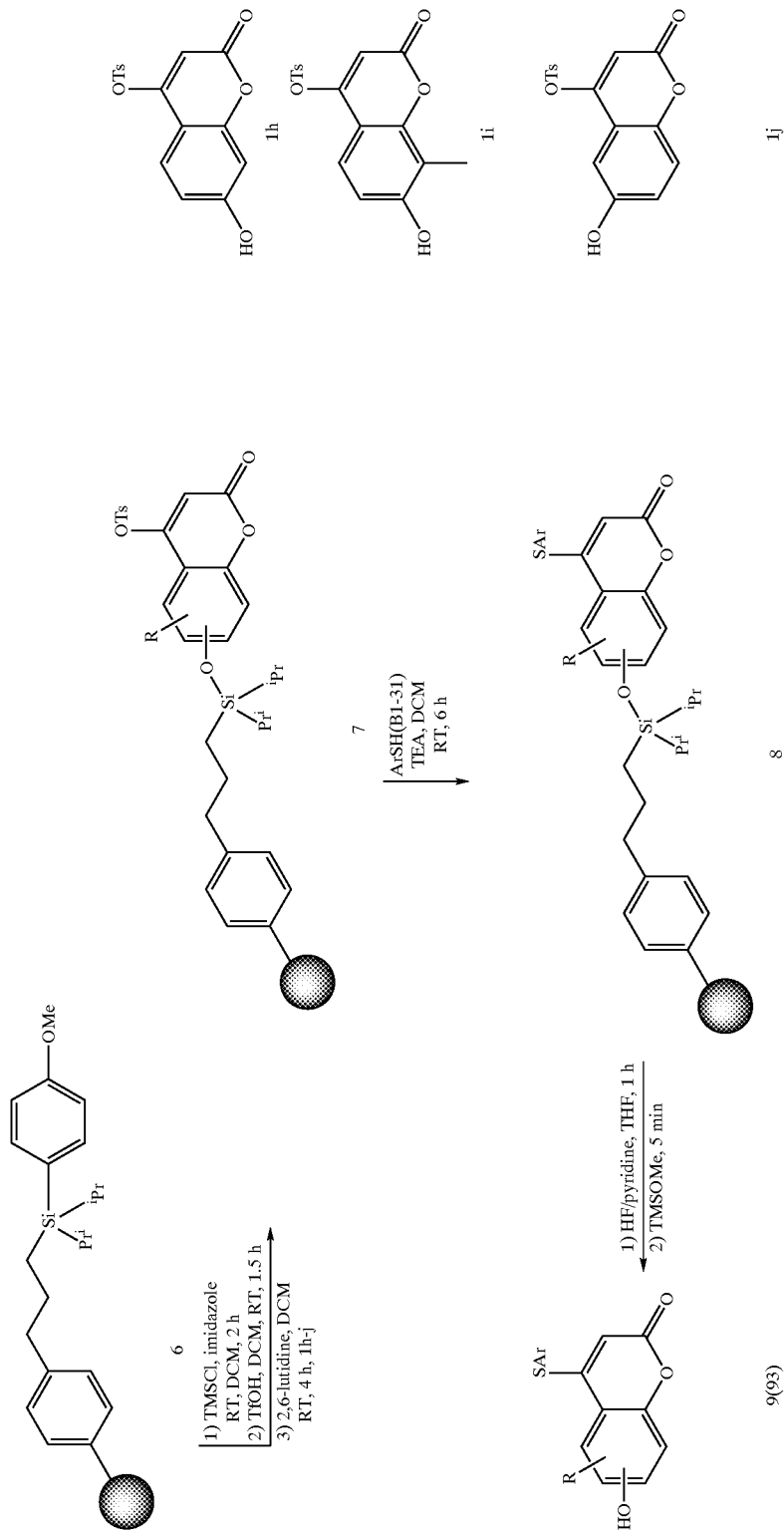

Loading of Hydroxycoumarin 1 h-j Onto Resin 6

Silicon-functionalized resin 6 that had been dried under high vacuum for 12 hours was weighed (200 mg) into a 10 mL polypropylene PD-10 column fitted with a Teflon stopcock and swollen in a solution of trimethylsilyl chloride (0.1 mL) and imidazole (20 mg) in $CH_2Cl_2$ (4 mL) under $N_2$ atmosphere for 2 h. The solvent was then drained under positive $N_2$ pressure, and 0.2 mL of trifluoromethanesulfonic acid in $CH_2Cl_2$ (4 mL) was added by syringe. The resin turned red/orange upon acid treatment and was then gently agitated for 1.5 hours while still under $N_2$ atmosphere. Once activation was completed, two $CH_2Cl_2$ washes removed excess acid. Then, 1h/1i/1j (2 equiv.) in 2,6-lutidine (0.8 mL) was added and the mixture resulted in a colorless resin. The beads are then gently agitated for an additional 4 hours under $N_2$ atmosphere. The beads were drained, exposed to atmosphere, and subjected to the following wash protocol: $CH_2Cl_2$ (5 mL, 2 h), DMF (5 mL, 2 h), MeOH (5 mL, 2 h), DMF (5 mL, 2 h), and $CH_2Cl_2$ (5 mL, 2 h). The resin 7 was air-dried for 3 h and then placed under high vacuum for 24 h to remove trace solvent and water.

Reaction of Thiols With Resin 7

General Procedure from 7 to 8: To a suspension of 7 (20 beads) with thiol (1.5 eq.) in dichloromethane (2 mL), triethylamine (2.0 eq.) was added at room temperature under air atmosphere. The beads are then gently agitated for an additional 6 hours under $N_2$ atmosphere. The beads were drained, exposed to atmosphere, and subjected to the following wash protocol: $CH_2Cl_2$ (2 mL, 2 h), DMF (2 mL, 2 h), MeOH (2 mL, 2 h), DMF (2 mL, 2 h), and $CH_2Cl_2$ (2 mL, 2 h). The resin 8 was then placed under high vacuum for 24 h to remove trace solvent and water.

Cleavage of 8 From Resin

Vacuum-dried resin 8 was transferred into a solvent-resistant scintillation vial and 200 μL of THF and 10 μL of HF/pyridine solution were added. The vial was sealed and agitated for 1 h, at which time 20 μL of methoxytrimethylsilane was added to quench unreacted HF.

The beads are further agitated for 30 min to ensure complete quenching. The solution was removed and the beads washed twice. All solvents were combined and concentrated in vacuo to afford the final product 9.

Those with skill in the art may recognize various modifications to the embodiments of the invention described and illustrated herein. Such modifications are intended to be covered by the spirit and scope of the present invention. That is, while the invention has been described in detail with reference to certain embodiments, it will be recognized by those skilled in the art that there are other embodiments of the invention within the spirit and scope of the claims.

What is claimed is:

1. A compound of the formula II,

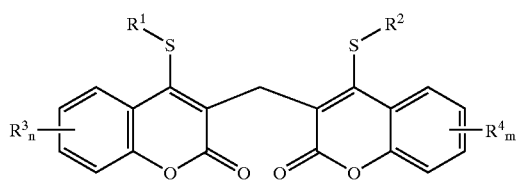

(II)

wherein $R^1$ and $R^2$ are independently selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

an unsubstituted or substituted alkyl group, wherein the substituted alkyl group may be substituted with one or more halogen, hydroxy, and lower alkoxy; and an unsubstituted or substituted cycloalkyl group, wherein the substituted cycloalkyl group may be substituted with one or more halogen, hydroxy, and lower alkoxy;

each $R^3$ and $R^4$ is independently selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or is a group of the formula

wherein Y and Q are independently selected from an aromatic group, O, S, —CR═CR—,

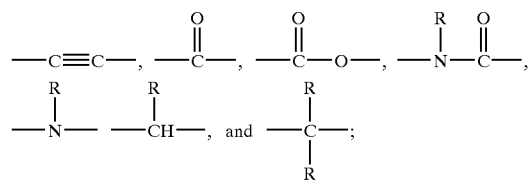

each R is independently selected from H or lower alkyl,

Z is selected from

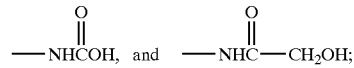

a, c and e are independently selected from values from 0 to 10;

b and d are independently selected from 0 and 1, provided that when a=0 then b=0, and when c=0 then d=0;

or $R^3$ or $R^4$ may occupy two adjacent positions to form a fused aromatic ring, n and m are independently selected from values between 0 and 4.

2. The compound of claim 1, wherein $R^3$ and $R^4$ are independently selected from fluorine or chlorine.

3. The compound of claim 1, wherein $R^3$ and $R^4$ are independently selected from hydroxy or methoxy.

4. A compound of the formula X

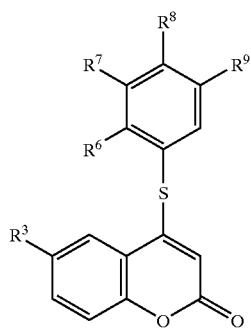

(X)

wherein $R^3$ is as described for the compound of formula I,
$R^6$ is selected from halogen, halogenated methyl, methoxy, and ethoxy;
$R^7$ is selected from H, halogen, halogenated methyl, methoxy, and ethoxy;
$R^8$ is selected from H, halogen, halogenated methyl, methoxy, and ethoxy, and
$R^9$ is selected from H, halogen, halogenated methyl, methoxy, and ethoxy.

5. The compound of claim 4, wherein $R^3$ is selected from halogen and lower alkoxy.

6. The compound of the claim 5, wherein $R^7$ is hydrogen.

7. The compound of claim 6, wherein $R^6$ is fluorine or chlorine, and one of $R^8$ and $R^9$ is a halogen, and the other is hydrogen.

8. The compound of claim 7, wherein the halogen is fluorine or chlorine.

9. The compound of claim 4, wherein the chemical structure is

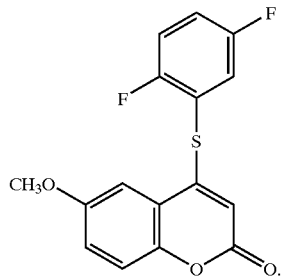

10. The compound of of claim 4, wherein the chemical structure is

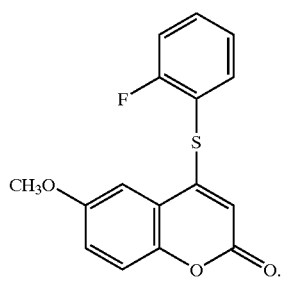

11. The compound of of claim 4, wherein the chemical structure is

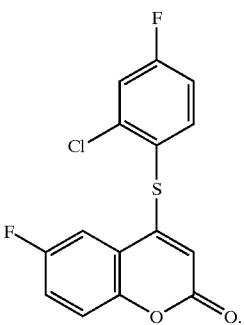

12. The compound of of claim 4, wherein the chemical structure is

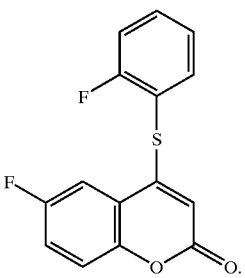

13. The compound of of claim 4, wherein the chemical structure is

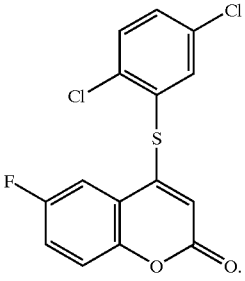

14. The compound of of claim 4, wherein the chemical structure is

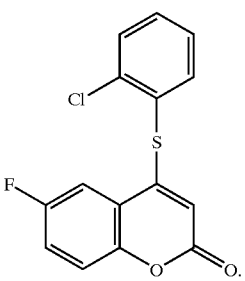

15. The compound of of claim 4, wherein the chemical structure is

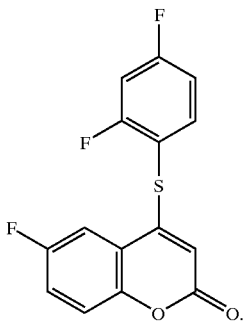

16. A process for the preparation of a compound of the formula I

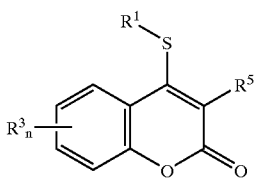
(I)

wherein a compound of the formula (IV)

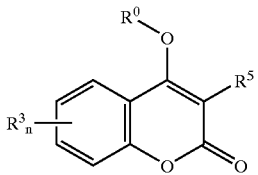
(IV)

is reacted with a thiol of the formula $R^1SH$, in the presence of a base,
  wherein $R_0$ in combination with the oxygen atom to which it is attached, forms a leaving group, and wherein
  $R^1$ is selected from
    an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
    a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
    an unsubstituted or substituted alkyl group, wherein the substituted alkyl group may be substituted with one or more halogen, hydroxy, and lower alkoxy; and
    an unsubstituted or substituted cycloalkyl group, wherein the substituted cycloalkyl group may be substituted with one or more halogen, hydroxy, and lower alkoxy;
  $R^3$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^3$ is a group of the formula

wherein Y and Q are independently selected from an aromatic group, O, S, —CR=CR—,

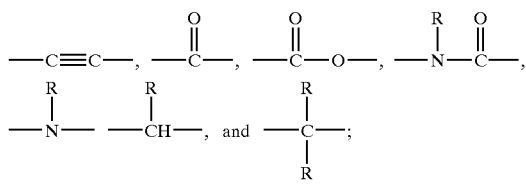

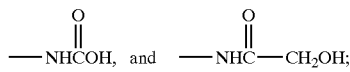

each R is independently selected from H or lower alkyl,
Z is selected from

H, —$CO_2R$, —OR, —SR, —$NR_2$,

—NHCOH, and —NHC—$CH_2OH$ (with C=O groups);

a, c and e are independently selected from values from 0 to 10;
b and d are independently selected from 0 and 1, provided that when a=0 then b=0, and when c=0 then d=0;
or $R^3$ may occupy two adjacent positions to form a fused aromatic ring, n is selected from values between 0 and 4;
$R^5$ is selected from hydrogen, lower alkyl, lower alkenyl, lower alkynyl, and lower aralkyl, each of which may be unsubstituted or substituted with one or more substituents selected from halogen, lower alkyl, and lower alkoxy, thio-lower alkyl $C_1$–$C_8$ acyl, lower alkyl ester, amide, and lower alkyl amide; or $R^1$ may be a group of the formula

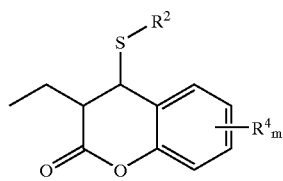

wherein
$R^2$ is selected from
  an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
  a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
  an unsubstituted or substituted alkyl group, wherein the substituted alkyl group may be substituted with one or more halogen, hydroxy, and lower alkoxy; and an unsubstituted or substituted cycloalkyl group, wherein the substituted cycloalkyl group may be substituted with one or more halogen, hydroxy, and lower alkoxy;

$R^4$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^4$ is a group of the formula $$Z-(CH_2)_a-Y_b-(CH_2)_c-Q_d-(CH_2)_e-$$

wherein Y and Q are independently selected from an aromatic group, O, S, —CR=CR—,

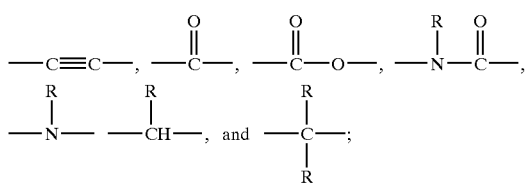

each R is independently selected from H or lower alkyl,

Z is selected from

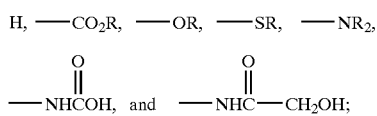

a, c and e are independently selected from values from 0 to 10;

b and d are independently selected from 0 and 1, provided that when a=0 then b=0, and when c=0 then d=0;

or $R^4$ may occupy two adjacent positions to form a fused aromatic ring, and, m is selected from values between 0 and 4.

17. The process of claim 16, wherein $R^0$ is tosyl and the base is an amine base.

18. The process of claim 17, wherein $R^5$ is hydrogen and $R^1$ is an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide.

19. The process of claim 18, wherein $R^1$ is unsubstituted or substituted phenyl, wherein the substituted phenyl may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide.

20. The process of claim 19, wherein $R^1$ is substituted phenyl wherein the substituted phenyl may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide.

21. The process of claim 20, wherein $R^1$ is substituted phenyl wherein the substituted phenyl may be substituted with one or more of halogen, hydroxy, lower alkyl, and lower alkoxy.

22. The process of claim 21, wherein $R^1$ is substituted phenyl wherein the substituted phenyl may be substituted with one or more of halogen and lower alkoxy.

23. A process for the preparation of a coumarin dimer of the formula II

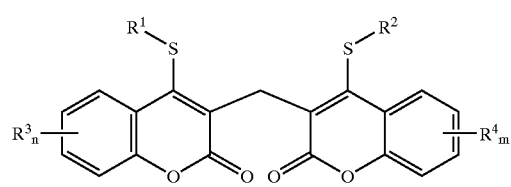

(II)

wherein a compound of the formula V

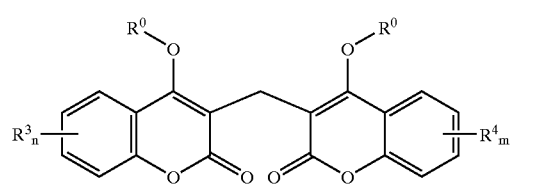

(V)

is reacted with a thiol of the formula $R^1$—SH or $R^2$—SH, in the presence of a base, wherein $R^0$, in combination with the oxygen atom to which it is attached, forms a leaving group, $R^1$, $R^2$, $R^3$, $R^4$, $R^5$, n and m are as defined in claim 1, and $R^1$ is the same as $R^2$.

24. The process of claim 23, wherein $R^0$ is tosyl and the base is an amine base.

25. A process for the preparation of a coumarin dimer of the formula II

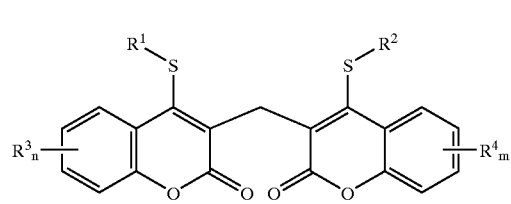

(II)

wherein a compound of the formula V

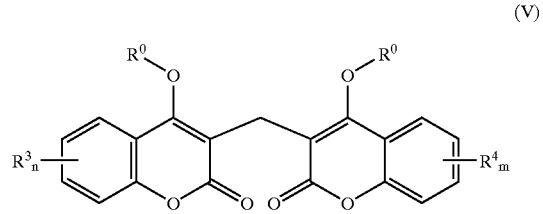

(V)

is reacted with a thiol of the formula $R^1$—SH in the presence of a base to give a compound of the formula VI

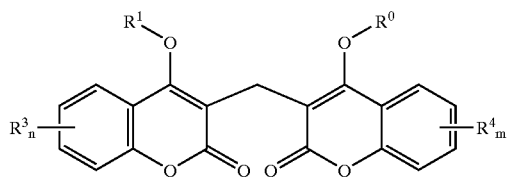

(VI)

and wherein the compound of the formula VI is further reacted with a thiol of the formula $R^2$—SH in the presence of a base to give a compound of the formula II, wherein $R^0$, in combination with the oxygen atom to which it is attached, forms a leaving group, $R^1$, $R^2$, $R^3$, $R^4$, $R^5$, n and m are as defined in claim 1, and $R^1$ is not the same as $R^2$.

26. The process of claim 25, wherein $R^0$ is tosyl and the base is an amine base.

* * * * *